(12) United States Patent
Yoo et al.

(10) Patent No.: US 10,254,232 B2
(45) Date of Patent: Apr. 9, 2019

(54) DEVICE FOR DETECTING ANALYZED OBJECT IN SPECIMEN AND METHOD THEREFOR

(71) Applicant: SUGENTECH, INC., Daejeon (KR)

(72) Inventors: Seungbum Yoo, Daejeon (KR); Eunkyung Kim, Daejeon (KR); Dong Gyu Lee, Daejeon (KR); Sang Hoon Oh, Jeonju-si (KR); Mi Jin Sohn, Daejeon (KR)

(73) Assignee: SUGENTECH, INC., Daejeon (KR)

( * ) Notice: Subject to any disclaimer, the term of this patent is extended or adjusted under 35 U.S.C. 154(b) by 494 days.

(21) Appl. No.: 14/786,225

(22) PCT Filed: Apr. 4, 2014

(86) PCT No.: PCT/KR2014/002914
§ 371 (c)(1),
(2) Date: Oct. 22, 2015

(87) PCT Pub. No.: WO2014/175577
PCT Pub. Date: Oct. 30, 2014

(65) Prior Publication Data
US 2016/0084768 A1    Mar. 24, 2016

(30) Foreign Application Priority Data

Apr. 23, 2013  (KR) .......................... 10-2013-0044971
Apr. 2, 2014   (KR) .......................... 10-2014-0039299

(51) Int. Cl.
*G01N 21/84*  (2006.01)
*G01N 21/75*  (2006.01)
*G01N 33/543*  (2006.01)

(52) U.S. Cl.
CPC .......... *G01N 21/75* (2013.01); *G01N 21/8483* (2013.01); *G01N 33/54366* (2013.01); *G01N 2201/062* (2013.01)

(58) Field of Classification Search
None
See application file for complete search history.

(56) References Cited

U.S. PATENT DOCUMENTS 5,073,484 A   12/1991  Swanson et al.
5,559,041 A   9/1996   Kang et al.
(Continued)

FOREIGN PATENT DOCUMENTS

CN   101650298 A   2/2010
CN   102483401 A   5/2012
(Continued)

OTHER PUBLICATIONS

International Searching Authority, International Search Report of PCT/KR2014/002914 dated Aug. 14, 2014 [PCT/ISA/210].
(Continued)

*Primary Examiner* — Rebecca L Martinez
(74) *Attorney, Agent, or Firm* — Sughrue Mion, PLLC

(57) ABSTRACT

A device for detecting analytes in a sample includes (a) n light source units generating light; (b) a reaction strip including (i) a test area illuminated with light from the light source unit and including a material reacting to the analytes, (ii) a control area illuminated with the light from the light source unit and including a control material, and (iii) a background area illuminated with the light from the light source unit; and (c) at least n+1 light receiving units detecting light emitted from the test area, the control area, and the background area of the reaction strip, respectively.

18 Claims, 12 Drawing Sheets

(56) References Cited

U.S. PATENT DOCUMENTS

| | | | |
|---|---|---|---|
| 5,580,794 | A | 12/1996 | Allen |
| 5,591,645 | A | 1/1997 | Rosenstein |
| 5,837,546 | A | 11/1998 | Allen et al. |
| 6,235,241 | B1 | 5/2001 | Catt et al. |
| 6,485,982 | B1 | 11/2002 | Charlton |
| 6,767,510 | B1 | 7/2004 | Buechler |
| 7,317,532 | B2 | 1/2008 | Sharrock et al. |
| 7,499,170 | B2 | 3/2009 | Sasaki et al. |
| 8,025,854 | B2 | 9/2011 | Ohman et al. |
| 2004/0071331 | A1 | 4/2004 | Lawless et al. |
| 2005/0037511 | A1* | 2/2005 | Sharrock .............. G01N 21/251 436/164 |
| 2010/0157300 | A1 | 6/2010 | Lee et al. |
| 2010/0172802 | A1 | 7/2010 | Sharrock et al. |
| 2012/0015448 | A1 | 1/2012 | Sharrock |
| 2012/0021531 | A1 | 1/2012 | Ellis et al. |
| 2012/0162653 | A1 | 6/2012 | Lee et al. |

FOREIGN PATENT DOCUMENTS

| | | | |
|---|---|---|---|
| JP | 2009-058507 | A | 3/2009 |
| JP | 2011-196825 | A | 10/2011 |
| KR | 10-2006-0048959 | A | 5/2006 |
| KR | 10-2011-0027013 | A | 3/2011 |

OTHER PUBLICATIONS

State Intellectual Property Office of People's Republic of China; Communication dated Dec. 28, 2016 in counterpart Application No. 201480023212.X.

* cited by examiner

[FIG. 1]
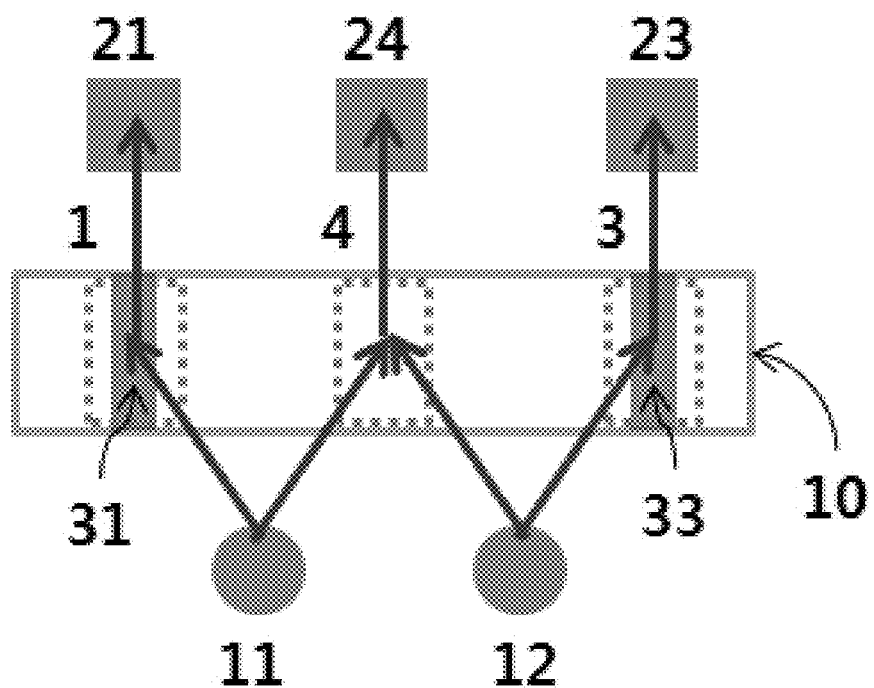

[FIG. 2]
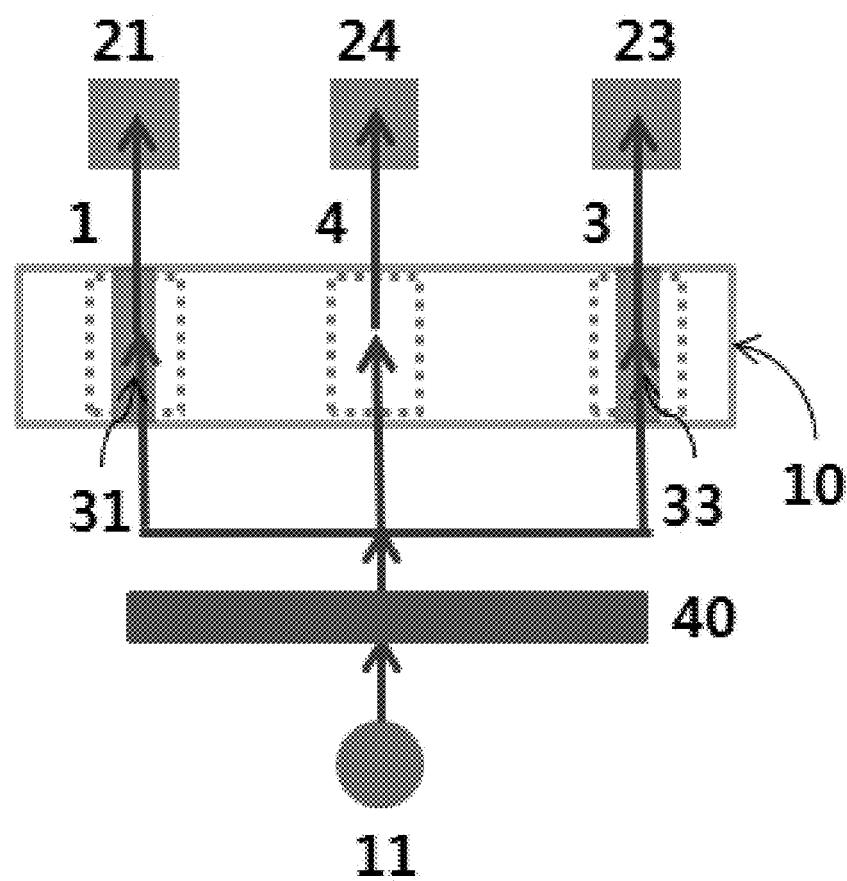

[FIG. 3]
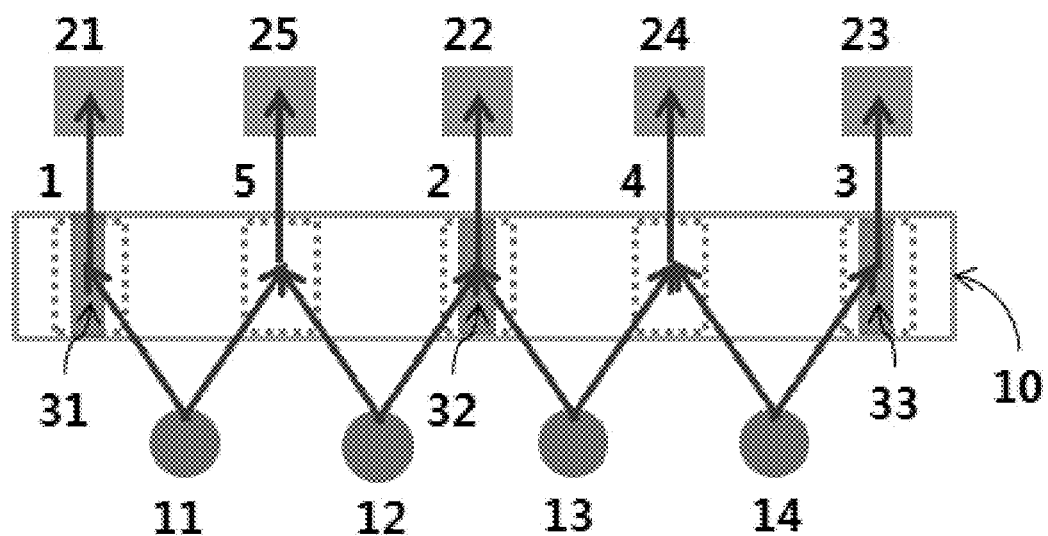

[FIG. 4]
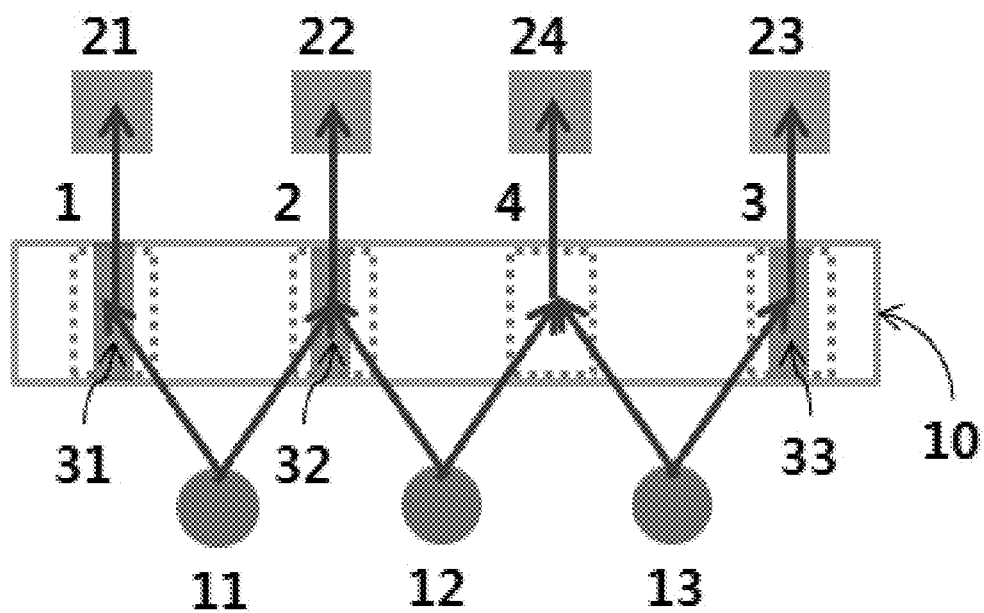

[FIG. 5]
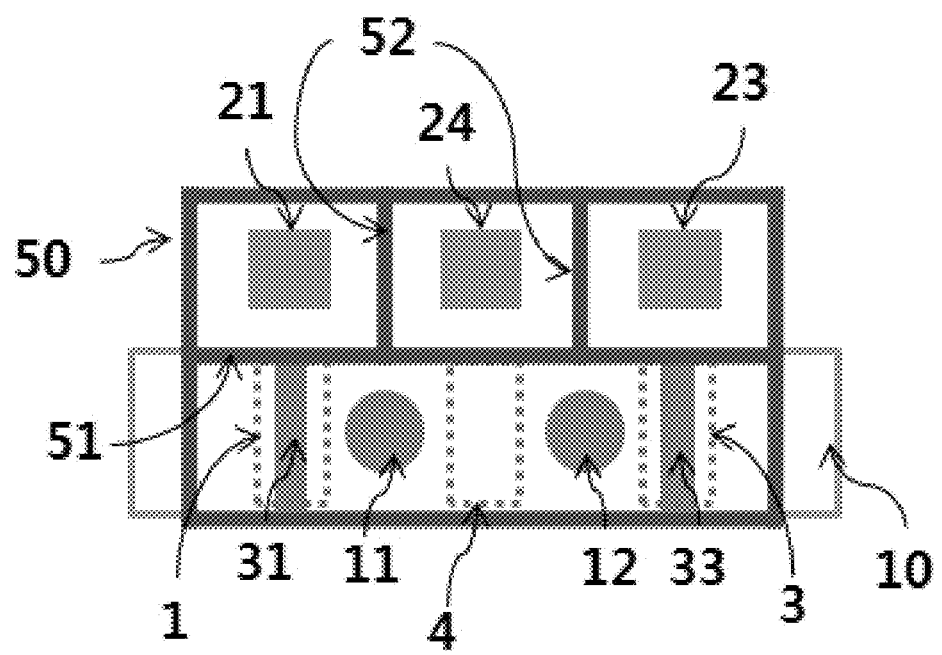

[FIG. 6]
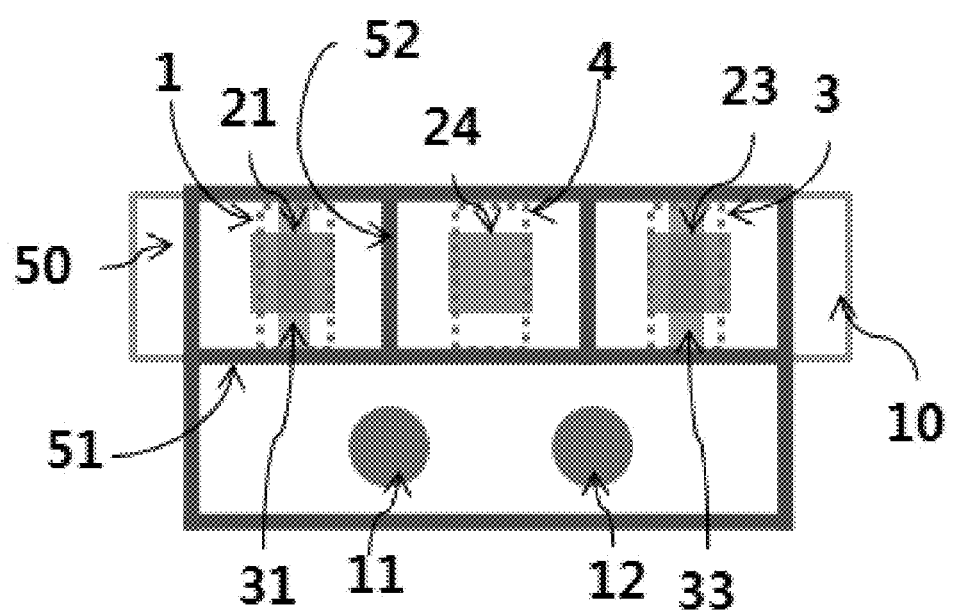

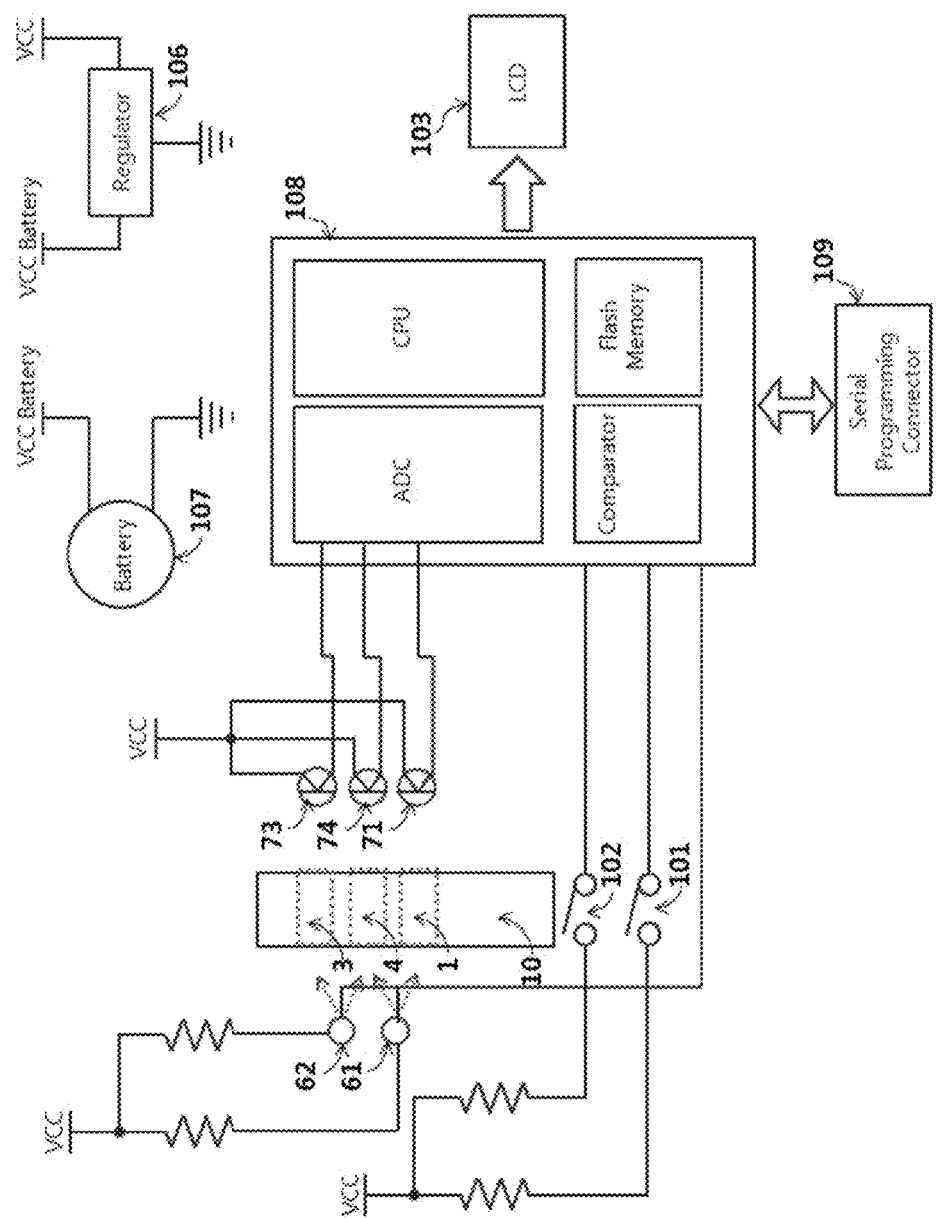
[FIG. 7]

[FIG. 8A]
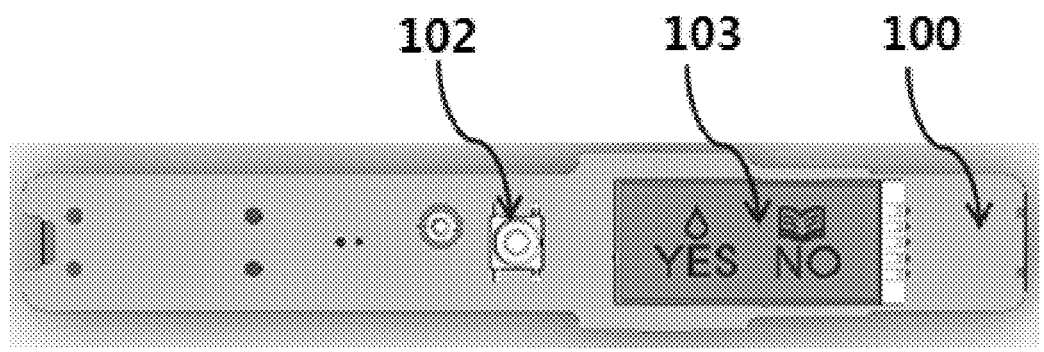

[FIG. 8B]
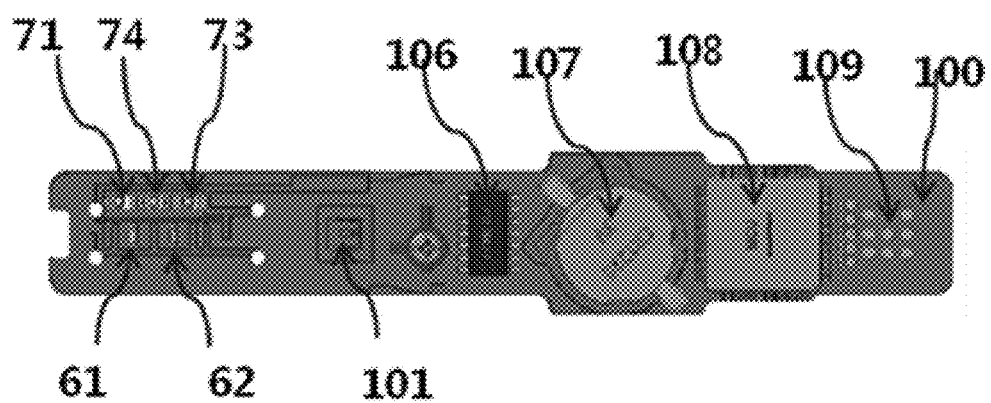

[FIG. 9A]
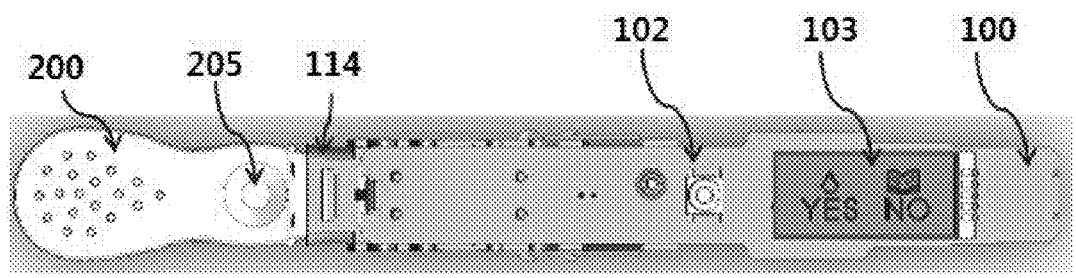
[FIG. 9B]
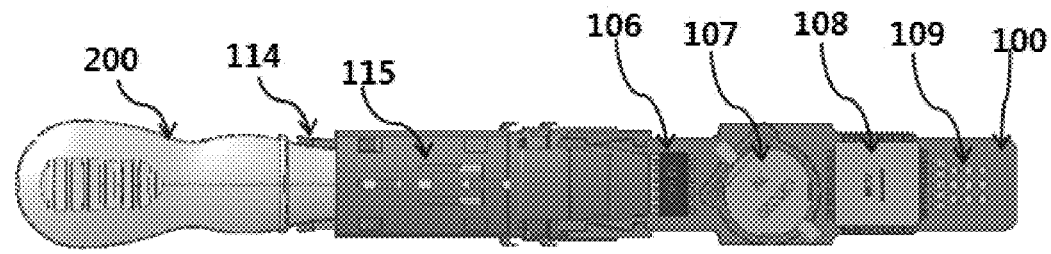

[FIG. 10A]
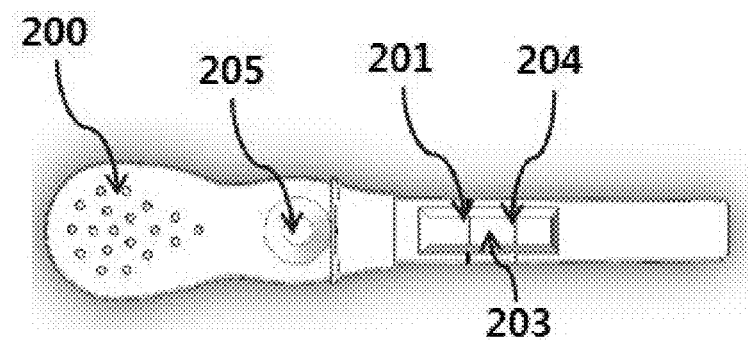
[FIG. 10B]
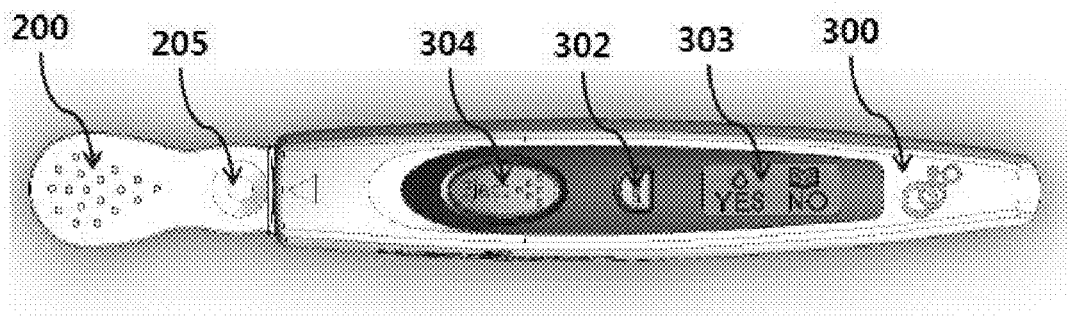

[FIG. 11]
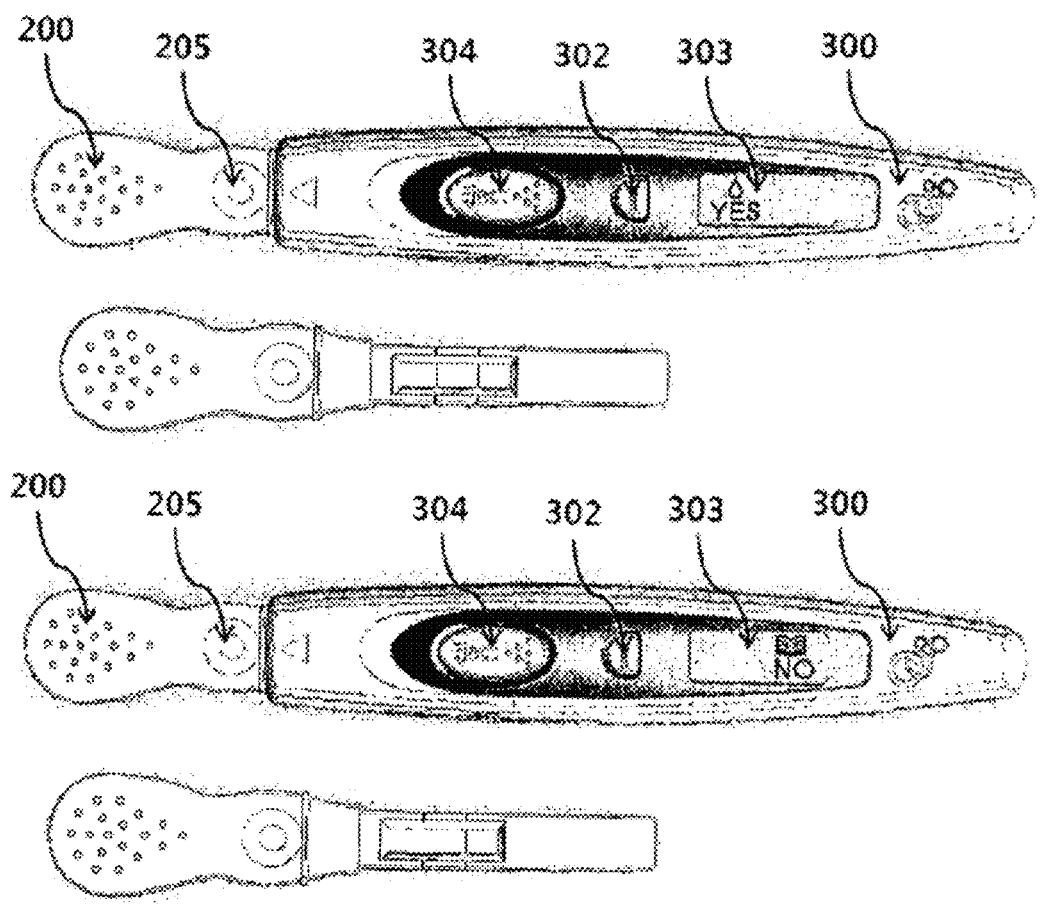

DEVICE FOR DETECTING ANALYZED OBJECT IN SPECIMEN AND METHOD THEREFOR

CROSS REFERENCE TO RELATED APPLICATIONS

This application is a National Stage of International Application No. PCT/KR2014/002914, filed Apr. 4, 2014, claiming priorities based on Korean Patent Application Nos. 10-2013-0044971, filed Apr. 23, 2013 and 10-2014-0039299, filed Apr. 2, 2014, the contents of all of which are incorporated herein by reference in their entirety.

TECHNICAL FIELD

The present invention relates to a device and method for detecting analytes in samples.

BACKGROUND ART

A material analysis by an optical method uses principles such as absorbance, fluorescence, phosphorescence, chemiluminescence, reflectance, turbidity, refraction, and scattering. To analyze biomaterials using the optical principles, labels such as radioactive materials, enzymes, fluorescent materials, chemiluminescent materials, gold nanoparticles, carbon black, latex particles, and quantum dots have been mostly used. Some cases of the optical reactions generated by the labels may be detected by human eyes. However analytical apparatus have to be used for more quantitative result. Upon the optical measurement of the biomaterials, signal strength is different depending on concentrations of the biomaterials. Most of the signals are measured by setting a background for noise. To enhance the accuracy, a signal-to-noise ratio needs to be efficiently measured. To measure the signal-to-noise ratio, generally, methods such as initial calibration before the reaction is generated and background calibration may be used alone or a combination thereof may be used.

As an analytical method of biomaterials using the above-mentioned principles, there are radioimmunoassay, enzyme-linked immunosorbent assay, particle agglutination assay, chemiluminescent immunoassay, real-time polymerase chain reaction, flow cytometry, immunochromatography, etc. These methods are not limited to the analysis of materials but have been used for a disease test or diagnosis, or the like. The analytical method of biomaterials may largely be classified into homogeneous assay of performing reaction only in a solution phase and a heterogeneous assay of separating analytes or labels onto the solid phase. As the solid phase used in the heterogeneous assay, there are a plastic plate or microparticles of a polystyrene material, a nitrocellulose membrane, magnetic particles, a glass slide, etc.

The immunochromatography measures a reaction by a scheme of developing the reaction using a porous membrane as the solid phase, the gold nanoparticles or the latex particles as the labels, etc., and accumulating the labels on a test line by an antigen-antibody reaction. The immunochromatography may have easy operability and easily observe the label visually in some cases, and therefore has been very variously used for self-testing of pregnancy or ovulation, drug-of-abuse test, hemoglobin A1c test, cardiovascular disease test, infectious disease test, etc. The immunochromatography includes a control area in which it is verified whether the reaction is correctly generated in addition to a test area in which the antigen-antibody reaction is tested. If the amount of samples is small or the reaction is not generated properly, a signal may not appear in the control area and if the concentrations of the analytes in the samples are high, the signal may be reduced or may not appear in the control area due to a prozone phenomenon. Technologies related to the immunochromatography have been known in several documents such as U.S. Pat. Nos. 5,073,484, 5,591,645, 5,559,041, and 6,485,982. In addition to the immunochromatography using the porous membrane, the microfluidics for performing micromachining on a plastic surface to make a predetermined structure in which a solution may move by a capillary action is also used as a point-of care testing. The relevant example has been described in several documents such as U.S. Pat. Nos. 6,767,510 and 8,025,854.

Meanwhile, when the gold nanoparticles, the colored latex particles, or the like are used as the labels, the reaction may be tested visually. However, the visual test may not obtain the quantitative results and the test results may differ by users. It is also possible to overlook abnormal reaction due to errors by a user or accurate measurement of the reaction time. Therefore, to meet a demand for an apparatus for analyzing them, various technologies and products have been developed.

As the analytical apparatus and the analytical method, there are an apparatus and a method for capturing an image of a reaction device using an analytical apparatus including image devices such as a charge-coupled device (CCD) and a complementary metal-oxide-semiconductor (CMOS) and then analyzing a signal and noise. Currently, many products using the analytical apparatus and the analytical method have been commercialized. However, the analytical apparatus and the analytical method are hardly miniaturized because the reaction device and an imaging device need to be spaced apart from each other at a predetermined distance to secure good image quality, need to use an image device and expensive components consuming relatively larger power for image analysis.

As another example, there are an analytical apparatus and an analytical method for measuring a signal and noise using a scheme of scanning the reaction device while moving a light source and a light receiving unit (photodetector) or a scheme of scanning the reaction device while fixing a light source and a light receiving unit, upon measuring the reaction in the reaction device. The scheme of scanning, by the light source and the light receiving unit, the reaction device may use one light source and one light receiving unit to reduce errors due to a deviation of the light source or the light receiving unit, but has a disadvantage in that it needs a driving apparatus for moving the reaction device or the optical unit, and therefore is hardly miniaturized and needs to calculate background noise based on a graph of the scanning of the reaction results, and therefore makes the process complicated and difficult. On the other hand, the scheme of scanning the reaction device while fixing the light source and the light receiving unit may be miniaturized and simplify the measurement, but has a disadvantage in that the light source and the light receiving unit capable of measuring the test area or the control area and the background noise may not be easily configured and the accurate test may be made only when deviations in components of the light source and the light receiving unit are solved.

U.S. Pat. Nos. 5,580,794 and 5,837,546 describe a disposal analytical apparatus for detecting reaction on a strip using reflectance by the light-emitting diode (LED) light sources and a light receiving unit. However, the patents do not disclose an optical arrangement and a method capable of measuring background noise and therefore cannot but calculate result values only by initial calibration. In this case, the above-mentioned patents are likely to cause wrong results due to interfering materials in samples having the color such as hemoglobin or bilirubin, and may have a limited applicable range.

U.S. Pat. No. 6,235,241 discloses an analytical apparatus for detecting reaction on a strip using transmission measurement by the light-emitting diode (LED) light sources and the light receiving units but does not disclose a method for effectively calibrating the light sources and background noise and has a problem in that the analytical apparatus may not be applied to a printed circuit board (PCB) on a plane in the case of using the transmission measurement and therefore may be complicated.

U.S. Pat. No. 7,317,532 discloses an optical arrangement for detecting reaction on a strip using reflectance by an LED light source and a light receiving unit. That is, the optical arrangement is configured in a scheme of illuminating light from the LED light source which is disposed in the middle among the three LED light sources arranged in a row to the background area between the control area and the test area and then detecting the illuminated light by two light receiving units for the control area and the test area and illuminating the light from the LED light sources for the control area and the test area to the strip to transfer the reflectance results to the light receiving unit and then calibrating and calculating the signal and the noise. However, the optical arrangement uses the light receiving unit of the control area and the test area instead of the light receiving unit for the background area and therefore has a limitation in the accurate calibration.

U.S. Pat. No. 7,499,170 discloses an analytical apparatus for detecting reaction using reflectance by setting a background area on a strip by one LED light source and two light receiving units but may detect a signal only in one test area without including the control area and therefore has a problem in that the apparatus may not be suitable for detection of test errors or various tests and may be applied to only one test area.

In addition, the above-mentioned analytical apparatuses and analytical methods may not suitably reduce deviations by calibrating the light sources and the light receiving unit on the equivalent condition.

Throughout the present specification, a number of articles and patent documents are referenced and the citation thereof is disclosed. The disclosure of the cited articles and patent documents is disclosed in the present specification as a whole and thus a level of the technical field to which the present invention belongs and the contents of the present invention will be more clearly described.

DISCLOSURE

Technical Problem

The present inventors have been tried to develop a miniaturized analytical apparatus and an analytical method for measuring a signal of reaction generated in the device for analyzing or detecting analytes in samples by the scheme in which a light source unit and a light receiving unit are fixed. As a result, the present inventors investigated a method for effectively analyzing the test device spatially divided into the test area, the control area, and the background area to optically indicate the reaction by using an analytical apparatus in which n light sources and at least n+1 light receiving units are constructed, thereby completing the present invention.

An object of the present invention is to provide a device for detecting analytes in samples.

Further, another object of the present invention is to provide a method for detecting analytes in samples.

Other objects and advantages of the present invention will be more clearly described below with reference to the detailed description, claims, and drawings of the present invention.

Technical Solution

In one general aspect, a device for detecting analytes in samples includes:

(a) n light sources generating light;

(b) a reaction strip including (i) a test area illuminated with light from the light source unit and including a material reacting to the analytes, (ii) a control area illuminated with the light from the light source unit and including a control material, and (iii) a background area illuminated with the light from the light source unit, in which the test area and the background area are illuminated with the same one light and the control area and the background area are illuminated with the same one light to let the test area and the control area share the background area and the light illuminated to the test area and the background area and the light illuminated to the control area and the background area are the same or different; and (c) at least n+1 light receiving units detecting light reflected from the test area, the control area, and the background area of the reaction strip, respectively, and arranged for the test area, the control area, and the background area respectively.

In another general aspect, a method for detecting analytes in samples includes:

(a) applying the samples to the device according to the present invention;

(b) determining final measurement values of the test area and the control area from light detected by at least n+1 light receiving units of the device; and (c) determining whether the analytes are present in the samples or the amount of analytes based on the final measurement values.

The present inventors have been tried to develop a miniaturized analytical apparatus and an analytical method for measuring a signal of reaction generated in the device for analyzing or detecting analytes in samples by a scheme in which a light source unit and a light receiving unit are fixed. As a result, the present inventors investigated a method for effectively analyzing the test device spatially divided into the test area, the control area, and the background area to optically indicate the reaction using an analytical apparatus in which n light source units and at least n+1 light receiving units are constructed.

The device according to the present invention may include the n light source units, the reaction strip including the test area, the control area, and the background area, and the at least n+1 light receiving units. n may be an integer equal to or more than 1.

The light source unit may include the light source generating light. According to the exemplary embodiment of the present invention, the light source unit may include known various light sources. For example, a light emitting diode (LED) and a laser may be used as the light source.

According to the present invention, the test area may include a material reacting to the analytes present in the samples. The reaction to the analytes may include various kinds of reactions and according to one implementation example, the reaction to the analytes may be binding.

According to one implementation example of the present invention, the material reacting to the analytes in the test area may be a capture agent binding to the analytes. An example of the capture agent used in the present invention may be protein, nucleic acid, lipid, carbohydrate, vitamin, or drug or a conjugated material thereof. According to one implementation example, the capture agent may be immobilized in the test area, in which the immobilization may be made by a method such as adsorption, hydrophobic interaction, a hydrogen bond, ionic interaction, and/or a covalent bond.

A detailed example of the capture agent used in the present invention may include an antibody, receptor, streptavidin (or avidin), aptamer, lectin, DNA, RNA, ligand, coenzyme, inorganic ion, cofactor, sugar, lipid, or substrate.

According to one implementation example of the present invention, when the material reacting to the analytes included in the test area is the capture agent, the device according to the present invention may further include a detection agent binding to the analytes. For example, when the capture agent is a capture antibody, the detection agent may be a detection antibody. In a rapid test kit using immunochromatography, the detection agent may be included in a conjugated pad.

According to one implementation example of the present invention, when there are the analytes in the samples, the detection agent may be conjugated with a label which may generate an optical signal indicating the presence of the analytes. The label may include various labels known in the art and may include, for example, enzymes (for example, alkaline phosphatase, β-galactosidase, horseradish peroxidase, β-glucosidase and cytochrome P450), gold particles (for example, gold nanoparticles), silver particles (for example, silver nanoparticles), fluorescent materials [for example, fluorescein, fluorescein Isothiocyanate (FITC), rhodamine 6G, rhodamine B, 6-carboxy-tetramethyl-rhodamine (TAMRA), Cy-3, Cy-5, Texas Red, Alexa Fluor, DAPI (4,6-diamidino-2-phenylindole), and Coumarin], latex particles containing fluorescent dye or pigment, chemiluminescent materials and coloring matters (for example, gardenia dye, eosin, phenol red, bromophenol blue, m-cresol purple, and bromocresol purple).

According to the present invention, the control area may be an area in which it is confirmed whether the reaction is generated properly. The control area may be constructed variously. For example, when the analytes are detected by sandwich immunoassay, the control area may be constructed using an antibody having binding capacity to a labeled detection antibody (for example, gold nanoparticle-detection antibody conjugate). If the method of the present invention is performed using the device of the present invention regardless of whether there are the analytes in the samples, the reaction may be generated in the control area. If the reaction is not generated in the control area, the results in the test area may be determined as errors.

When the present invention uses the detection agent, the capture agent included in the control area may be a material binding to the detection agent. For example, when the detection agent is the detection antibody, the capture agent may be an antibody having the binding capacity to the detection antibody.

According to one implementation example of the present invention, the background area according to the present invention may have the same environment as the background environment (that is, environment other than the material used for the reaction in the test area and the control area) of the test area and the control area. For example, when the test area and the control area are formed on a white nitrocellulose membrane, the background area may be formed on the white nitrocellulose membrane, which may be used as itself without any treatment or with special treatment for reducing non-specific reaction or solution development. According to the detailed exemplary embodiment of the present invention, the background area may use white color to minimize the light absorption.

The present invention includes the reaction strip including the background area to which the light from the light source unit is illuminated, in which the test area and the background area are illuminated with the same one light and the control area and the background area are illuminated with the same one light to let the test area and the control area share the background area and the light illuminated to the test area and the background area and the light illuminated to the control area and the background area may be the same or different.

According to an exemplary embodiment of the present invention, the light illuminated to the test area and the background area and the light illuminated to the control area and the background area may be the same. In the present specification, the term "same light" has a meaning including light emitted from the one light source unit and light having the same optical characteristics (for example, wavelength).

The reaction strip including the test area, the background area, and the control area may be made of various materials of a porous membrane such as nitrocellulose, cellulose paper, glass fiber, plastic, glass, etc. The flow and reaction of the samples and the detection agent in the reaction strip may be performed by various schemes such as chromatography, a capillary phenomenon, mixing by stirring, and diffusion.

At least n+1 light receiving units configuring the device of the present invention may detect the light reflected from the test area, the control area, and the background area of the reaction strip, respectively, and may be arranged for the test area, the control area, and the background area, respectively. That is, the light emitted from the test area, the control area, and the background area, respectively, may be detected by each of the light receiving units.

The best feature of the present invention is that the n light source units and the at least n+1 light receiving units are used. Due to the features of the configuration, the following various technical advantages are obtained.

For example, the photodiode, the phototransistor, and the photoresistor may be used as the light receiving unit.

The device of the present invention may be constructed for multiplex detection in which the test areas are configured in plural. Meanwhile, for the description of the operation scheme of the present invention, if it is assumed that the present invention detects one kind of analytes, the reaction strip may include one test area, control area, and background area, respectively. In this case, the light sources may include a first light source unit and a second light source unit, the light receiving unit may include a first light receiving unit, a second light receiving unit, and a third light receiving unit and the light from the first light source unit may illuminate the test area and the background area, the light from the second light source unit may illuminate the background area and the control area, and the light reflected from the test area, the background area, and the control area may be detected by the first light receiving unit, the second light receiving unit, and the third receiving unit, respectively (see FIG. 1). By this scheme, the test area and the control area may share the background area, such that the background noise may be removed by calibration.

One of the advantages of the device of the present invention may be constructed well to detect the multiplex reaction in which the test areas are configured in plural. According to one implementation example of the present invention, in the device of the present invention, the test area, the background area, or the test area and the background area may be at least two. Even the device for the multiplex detection may be sufficiently performed using one control area. According to one implementation example of the present invention, the calibrations for one of at least two test areas and the control area may share the reaction of the background area.

The device of the present invention including the plurality of test areas may be manufactured by various schemes unless it deviates from the principle that it shares the background area (see FIGS. 3 and 4).

As illustrated in FIG. 3, the device of the present invention may be configured to include four light source units, two test areas, two background areas, one control area, and five light receiving units. The calibrations for the first test area and the second test area may share the reaction of the first background area and the calibrations for thesecond test area and the control area may share the reaction of the second background area.

As another example, the device of the present invention illustrated in FIG. 4 may be configured to include three light source units, two test areas, one background area, one control area, and four light receiving units. The calibrations for the second test area and the control area may share the reaction of the background area.

According to one implementation example of the present invention, the device of the present invention may further include a processor calibrating values detected by the light receiving unit for the background area to be the same value by using the value (initial value) detected by the light receiving unit before the reaction is generated in the test area and the control area and obtaining a calibration value before the reaction of the test area and the control area by using the calibration value before the reaction of the background area and the values detected by the light receiving unit for the test area and the control area.

According to one implementation example of the present invention, the processor may additionally perform a process of obtaining a calibration value after the reaction of the test area and the control area by using the calibration value before the reaction of the background area or the calibration value after the reaction and the values detected after the reaction in the light receiving unit for the test area and the control area, after the reaction is generated in the test area and the control area.

According to one implementation example of the present invention, the processor may additionally perform a process of determining a value of an equation using the calibration value before the reaction and the calibration value after the reaction in the test area and the control area as a final measurement value of the test area and the control area.

The equation used to obtain the final measurement value may be arbitrarily set. An example of the simple equation is "the final measurement value of the test area=the calibration value before the reaction of the test area-the calibration value after the reaction of the test area", "the final measurement value of the test area=the calibration value before the reaction of the test area/the calibration value after the reaction of the test area", "the final measurement value of the control area=the calibration value before the reaction of the control area-the calibration value after the reaction of the control area", or "the final measurement value of the control area=the calibration value before the reaction of the control area/the calibration value after the reaction of the control area".

According to one implementation example of the present invention, the processor may additionally perform a process of comparing the final measurement value with a predetermined cut-off value to qualitatively determine whether the analytes are present in the samples.

According to one implementation example of the present invention, the processor may additionally perform a process of substituting the final measurement value into a previously calculated quantification curve to quantitatively analyze the analytes in the samples.

The calibration method and the qualitative and quantitative analytical methods according to the present invention will be described in detail in the following exemplary embodiments.

According to one implementation example of the present invention, the light source unit may additionally include the optical splitter. As illustrated in FIG. 2, when the optical splitter is used, one light source unit may illuminate light to the test area, the control area, and the background area under the equivalent conditions. According to the present invention, generally, when the number of light source units is n, the number of light receiving units may be n+1. Meanwhile, if the present invention uses the optical splitter, when the number of light source units is n, the number of light receiving units exceeds n+1.

According to one implementation example of the present invention, the device of the present invention may further include a microcontroller (for example, a central processing unit (CPU), a flash memory, an analog-to-digital converter (ADC), and a comparator), a voltage regulator, and/or a display (for example, LCD) for measurement control and calculation, in addition to the light source unit, the reaction strip, and the light receiving unit. According to one implementation example, the device of the present invention may further include a detector switch, a battery, and/or a serial programming connector.

The present invention may be used to qualitatively or quantitatively detect the analytes.

The present invention may be applied well for multiplex detection to detect the analytes in the samples.

An example of the samples which may be used in the present invention may include blood, plasma, serum, urine, lymph, bone marrow, saliva, milk, ocular fluid, semen, brain extracts, spinal fluid, synovial fluid, thymic fluid, ascites, amniotic fluid, cell tissue liquid, buffer solution, tap water, polluted water, sewage, or ground water.

According to the present invention, the analytes to be analyzed may include proteins, peptides, nucleotide sequences, genes, lipids, carbohydrates, vitamins, drugs, organic compounds, inorganic matters, and liquefied gas but are not limited thereto.

The present invention may be used in various fields such as diagnosis and prediction of disease, health care, paternity confirmation, physical constitution confirmation, fermentation engineering, biomedical engineering, food safety test, environmental analysis, cosmetics analysis and compound analysis.

Advantageous Effects

The features and advantages of the present invention are as follows.

(a) The best feature of the present invention is that n light source units and at least n+1 light receiving units are used.

(b) According to the exemplary embodiments of the present invention, it is possible to accurately measure analytes by effectively calibrating the background noise.

(c) According to the exemplary embodiments of the present invention, it is possible to qualitatively and quantitatively analyze the analytes in samples.

(d) The present invention may indicate the excellent operability even in the multiplex detection (at least two test areas) for analyzing two or more analytes in samples.

DESCRIPTION OF DRAWINGS

FIG. 1 is a diagram schematically illustrating a detailed implementation example of a device of the present invention. 1: Test area, 3: Control area, 4: Background area, 10: Reaction strip, 11: First light source unit, 12: Second light source unit, 21: First light receiving unit, 24: Second light receiving unit, 23: Third light receiving unit, 31: Test line, 33: Control line.

FIG. 2 is a diagram schematically illustrating another implementation example of the device of the present invention using an optical splitter. 1: Test area, 3: Control area, 4: Background area, 10: Reaction strip, 11: Light source unit, 21: First light receiving unit, 24: Second light receiving unit, 23: Third light receiving unit, 31: Test line, 33: Control line, 40: Optical splitter.

FIG. 3 is a diagram schematically illustrating the implementation example of the device of the present invention having two test areas, two background areas, and one control area. 1: First test area, 2: Second test area, 3: Control area, 5: First background area, 4: Second background area, 10: Reaction strip, 11: First light source unit, 12: Second light source unit, 13: Third light source unit, 14: Fourth light source unit, 21: First light receiving unit, 25: Second light receiving unit, 22: Third light receiving unit, 24: Fourth light receiving unit, 23: Fifth light receiving unit, 31, 32: Test line, 33: Control line.

FIG. 4 is a diagram schematically illustrating the implementation example of the device of the present invention having two test areas, one background area, and one control area. 1: First test area, 2: Second test area, 3: Control area, 4: Background area, 10: Reaction strip, 11: First light source unit, 12: Second light source unit, 13: Third light source unit, 21: First light receiving unit, 22: Second light receiving unit, 24: Third light receiving unit, 23: Fourth light receiving unit, 31, 32: Test line, 33: Control line.

FIG. 5 is a diagram schematically illustrating a detailed implementation example of an assembly of the device of the present invention, in which two light source units each are positioned thereover, corresponding to the test area and the control area. 10: Reaction strip, 11: First light source unit, 12: Second light source unit, 21: First light receiving unit, 24: Second light receiving unit, 23: Third light receiving unit, 31: Test line, 33: Control line, 50: Mechanism unit, 51, 52: Barrier rib.

FIG. 6 is a diagram schematically illustrating another implementation example of the assembly of the device of the present invention, in which three light source units each are positioned thereover, corresponding to the test area, the background area, and the control area. 10: Reaction strip, 11: First light source unit, 12: Second light source unit, 21: First light receiving unit, 24: Second light receiving unit, 23: Third light receiving unit, 31: Test line, 33: Control line, 50: Mechanism unit, 51, 52: Barrier rib.

FIG. 7 is a diagram schematically illustrating a configuration and a circuit according to the detailed implementation example of the device of the present invention. 61, 62: LED, 71, 73, 74: Phototransistor, 101: Detector switch, 102: Start switch, 103: Liquid crystal display (LCD), 106: Voltage regulator, 107: Coin battery, 108: Microcontroller, 109: Serial programming connector.

FIGS. 8A and 8B are diagrams schematically illustrating a printed circuit board (PCB) according to the detailed implementation example of the device of the present invention, in which FIG. 8A illustrates that the LCD and the start switch are positioned at the upper portion of the PCB and FIG. 8B illustrates that the microcontroller, the battery, the light source unit, and the light receiving unit are positioned at the lower portion of the PCB. 100: PCB, 102: Start switch, 103: Liquid crystal display (LCD), 106: Voltage regulator, 107: Coin battery, 108: Microcontroller, 109: Serial programming connector.

FIGS. 9A and 9B are diagrams illustrating an upper portion and a lower portion of the PCB having a form in which a reaction strip housing according to the detailed implementation example of the device of the present invention is inserted into a mechanism unit, in which the mechanism unit is positioned at the lower portion of the PCB. 100: PCB, 102: Start switch, 103: Liquid crystal display (LCD), 106: Voltage regulator, 107: Coin battery, 108: Microcontroller, 109: Serial programming connector, 114, 115: Mechanism unit, 200: Reaction strip housing, 205: Sample dripping unit.

FIG. 10A is a diagram schematically illustrating the reaction strip housing according to the detailed implementation example of the device of the present invention and FIG. 10B is a diagram schematically illustrating a measuring device into which the strip housing is inserted. 200: Reaction strip housing, 201: Test line, 203: Background area, 204: Control line, 205: Sample loading unit, 300: Measurement device housing, 302: Start button, 303: LCD, 304: Eject button.

FIG. 11 is a diagram illustrating results measured by using a luteinizing hormone (LH) test strip according to the detailed implementation example of the device according to the exemplary embodiment of the present invention.

BEST MODE

Hereinafter, exemplary embodiments of the present invention will be described in more detail. These exemplary embodiments are to describe in more detail the present invention and it will be apparent to those skilled in the art that the scope of the present invention is not limited to these exemplary embodiments.

Exemplary Embodiments

A detailed exemplary embodiment of the present invention is as follows.

The best feature of the present invention is that light receiving units 21, 22, 23, 24, and 25 are arranged to be at least one more than light source units 11, 12, 13, and 14. That is, if n light source units 11, 12, 13, and 14 are used, the light receiving units 21, 22, 23, 24, and are configured of at least n+1. According to a configuration scheme of a device of the present invention, light from one light source unit is illuminated to a test area and a background area or a control area and a background area (FIGS. 1 and 3) or two test areas (FIG. 4) under the equivalent condition.

In the case of using the optical splitter 40, one light source may illuminate light to the test area 1, the control area 3, and the background area 4 under the equivalent conditions (FIG. 2).

The light receiving units 21, 22, 23, 24, and 25 need to be arranged to one to one correspond to the test areas 1 and 2 and the control area 3 so as to detect an optical reaction to the illuminated light and need to be arranged to one to one correspond to at least one background area 4 and 5.

According to the exemplary embodiment of the present invention, the test areas 1 and 2, the control area 3, and the background areas 4 and 5 of the device may be standardized by initial calibration of n light source units 11, 12, 13, and 14 and at least n+1 light receiving units 21, 22, 23, 24, and 25. That is, if light from the light source in the device before the reaction is generated is illuminated to a combination of the test areas 1 and 2, the control area 3, and the background areas 4 and 5 under the equivalent conditions, the light receiving units 21, 22, 23, 24, and 25 one to one corresponding to each area detect light. In this case, two areas are illuminated with light from one light source under the equivalent conditions and each of the light source units 11, 12, 13, and 14 shares a common area, such that the standardization may be made.

FIG. 1 illustrates an example of the analytical method. The two light source units 11 and 12 illuminate light to the test area 1, the control area 3, and the background area 4 on an immunochromatography strip 10 configured of one test line 31 and one control line 33 under the equivalent condition and thus the reflected light is detected by three light receiving units 21, 23, and 24. In this configuration, the first light source unit 11 illuminates light to the test area 1 and the background area 4 and thus the reflected light is detected by the first light receiving unit 21 for the test area 1 and the second light receiving area 24 for the background area 4. The second light source unit 12 illuminates light to the control area 3 and the background area 4 and thus the reflected light is detected by the second light receiving unit 23 and the third light receiving unit 24.

FIG. 7 is a diagram schematically illustrating a configuration and a circuit of the device using the light source unit and the light receiving unit, according to the detailed implementation example of the device of the present invention, FIGS. 8A and 8B are diagrams schematically illustrating an upper portion and a lower portion of a printed circuit board (PCB) according to the detailed implementation example of the device of the present invention, FIGS. 9A and 9B are diagrams schematically illustrating the PCB having a form in which a reaction strip housing according to the detailed implementation example of the device of the present invention is inserted into a mechanism unit, and FIGS. 10A and 10B are diagrams schematically illustrating the reaction strip housing according to the detailed implementation example of the device of the present invention and a measurement device into which the strip housing is inserted. According to the detailed implementation example of the present invention, components such as light source units 61 and 62, light receiving units 71, 73, and 74, a microcontroller 108, a battery 107, an LCD 103, and switches 101 and 103 are positioned on a PCB 100. Various kinds of light source units such as red, green, blue, or three colors may be used and according to the detailed implementation example of the present invention, a green light-emitting diode (LED) is used. As the light receiving unit, a phototransistor or a photodiode may be used and according to the detailed implementation example of the present invention, the phototransistor is used. Light from the light source unit is irradiated to and reflected from the test device and then a signal is received by the light receiving unit and a calculation of the signal and a control of the reaction are made by the microcontroller 108. According to the detailed implementation example of the present invention, the microcontroller may be implemented at low power and is configured to include a central processing unit (CPU) for calculation, an analog-to-digital converter (ADC), an analog comparator, a flash memory, an LCD driver, a serial communication interface, etc. According to the detailed implementation example of the present invention, a voltage is constantly maintained using a voltage regulator 106, thereby obtaining more stable results. According to the detailed implementation example of the present invention, if a reaction device 200 is inserted into a measurement device, a circuit is connected by the detector switch 101 and thus power is supplied from battery 107, thereby turning on the LCD 103. The LCD may be configured using various characters or diagrams and may display a progress of test and result errors. If power is supplied by a tact switch, an operation of the light source unit and the light receiving unit may be applied by various methods and according to the detailed implementation example of the present invention, after a start button 302 is pressed to turn on the start switch 103, the light source unit and the light receiving unit are operated. According to the detailed implementation example of the present invention, it may be connected to external devices such as a computer through the serial programming connector 109 to analyze the reaction. The test device performing the measurement is separated by pressing a ejecting button 304.

A device strip before the reaction is generated is a white nitrocellulose membrane and is illuminated with light rays under the equivalent conditions, and light from the first light source unit 11 and the second light source unit are illuminated to the common background area 4 and therefore two measurement values may be standardized by several schemes. As described above, the standardization scheme is applied to the control area 3 and thus values for the first light receiving unit 21 and the third light receiving unit 23 may also be standardized, such that although each of the light sources and the light receiving units uses separate components, all of them may be standardized before the reaction to perform the initial calibration.

After the reaction is generated, a test line 31 of the test area 1 defines signal strength by a label and a control line 33 t appears a signal by the label when the reaction is performed normally. The strip after the reaction is generated is not in an equivalent state and values measured after the reaction from the initial calibration measured before the reaction may be quantified by several schemes.

An example of the calibration method according to the present invention will be described below.

As shown in the following Table 1, the measurement values obtained by the device of FIG. 1 are defined and then the initial calibration, the background calibration, etc., may be performed as follows.

TABLE 1

| Light source | Light receiving unit | Measurement value of light receiving unit before reaction | | Measurement value of light receiving unit after reaction | |
|---|---|---|---|---|---|
| | | Before calibration | After calibration | Before calibration | After calibration |
| 11 | 21 | $T_0$ | $T'_0$ | $T_t$ | $T'_t$ |
| 11 | 24 | $BT_0$ | $BT'_0$ | $BT_t$ | $BT'_t$ |

TABLE 1-continued

| Light source | Light receiving unit | Measurement value of light receiving unit before reaction | | Measurement value of light receiving unit after reaction | |
|---|---|---|---|---|---|
| | | Before calibration | After calibration | Before calibration | After calibration |
| 12 | 23 | $C_0$ | $C'_0$ | $C_t$ | $C'_t$ |
| 12 | 24 | $BC_0$ | $BC'_0$ | $BC_t$ | $BC'_t$ |

(a) Before the reaction is generated, if a constant a for the initial calibration is reflected, $BC_0$ and $BT_0$ may be calibrated to be the same value to calibrate the light source unit and if constants b and c are reflected to the so calibrated light source unit, all the light receiving units may be calibrated. Therefore, the measurement values in the test area 1 and the control area 3 will be calculated as follows.

$$a = BC_0/BT_0, b = BT_0/T_0,$$

$$c = BC_0/C_0$$

$$BT'_0 = BT_0 \times a, T'_0 = T_0 \times a \times b, C'_0 = C_0 \times c$$

(b) After the reaction is generated, calibration constants a, b, and c of the light source unit and the light receiving unit are reflected to calculate the measurement values in the test area 1 and the control area 3 as follows.

$$BT'_t = BT_t \times a, T'_t = T_t \times a \times b, C'_t = C_t \times c$$

(c) The calibrated values may calculate a final measurement value TI of the test area 1 and a final measurement value CI of the control area 3 as follows by using a difference or a ratio between before the reaction and after the reaction.

$$TI = T'_0 - T'_t, CI = C'_0 - C'_t, \text{ or } TI = T'_t/T'_0, CI = C'_t/C'_0$$

Another example of the calibration method according to the present invention will be described below.

As shown in the above Table 1, the measurement values obtained by the device of FIG. 1 are defined and then the initial calibration, the background calibration, etc., may be performed as follows.

(a) Before the reaction is generated, the $BC_0$ and the $BT_0$ are averaged and calibrated to be the same value, such that the light source unit may be calibrated and the light receiving unit for the so calibrated light source unit may be calibrated. Therefore, the measurement values in the test area 1 and the control area 3 will be as follows.

$$BT'_0 = CT'_0 = (BT_0 + BC_0)/2$$

$$T'_0 = T_0 \times BT'_0/BT_0, C'_0 = C_0 \times BC'_0/BC_0$$

(b) After the reaction is generated, the light source unit and the light receiving unit are calibrated to calculate the measurement values in the test area 1 and the control area 3 as follows.

$$BT'_t = CT'_t = (BT_t + BC_t)/2$$

$$T'_t = T_t \times BT'_t/BT_t, C'_t = C_t \times BC'_t/BC_t$$

(c) The calibrated values may calculate a final measurement value TI of the test area 1 and a final measurement value CI of the control area 3 as follows by using a difference between before the reaction and after the reaction or a ratio.

$$TI = T'_0 - T'_t, CI = C'_0 - C'_t \text{ or } TI = T'_t/T'_0$$

$$CI = C'_t/C'_0$$

The calculated measurement values may be used for qualitative analysis depending on a predetermined cutoff value or are substituted into the a previously calculated quantitative curve, thereby calculating a quantitative value. In this case, the measured value in the control area may be used to verify the reaction or analyze a prozone phenomenon and may be used to input a specific value to reduce a deviation in the reaction strip and then calibrate the value of the test area depending on the input value.

FIG. 11 is a diagram illustrating results measured by using a luteinizing hormone (LH) test strip manufactured according to the exemplary embodiment of the present invention. The luteinizing hormone (LH) test strip is manufactured by immobilizing goat anti-alpha-LH antibody (Arista Biologicals) as the test line and goat anti-mouse IgG antibody (Arista Biologicals) as the control line onto the nitrocellulose membrane (Millipore). The background area is configured of the white nitrocellulose membrane and may be used as it is without any treatment or with special treatment for reducing non-specific reaction or solution development. According to the detailed implementation example of the present invention, the background area may use white color to minimize the light absorption. A mouse anti-beta LH colloidal gold conjugate (Arista Biologicals) is used to detect the luteinizing hormone and is dripped and dried onto a conjugate pad (Millipore). A sample pad (Millipore), the conjugate pad, the nitrocellulose membrane, and an absorption pad (Millipore) overlap each other, are cut by a length of 4 mm, are assembled in the housing, and then the sample adds the sample to the sample loading unit of the housing, thereby performing the test. A second image of FIG. 11 indicates that the LH in the samples is present over a cutoff, as the reaction is generated in both of the test line and the control line. A fourth image of FIG. 11 indicates that the LH in the samples is present under a cutoff, as the reaction is generated in only the control line. The light from the light source unit is illuminated to the test area, the control area, and the background area, reflected, and then detected by the light receiving unit. In this case, if the detection result is positive depending on a predetermined cutoff value, YES (first image of FIG. 11) is displayed on the LCD and if the detection result is negative, NO (third image of FIG. 11) is displayed on the LCD.

According to the present invention, each measurement value is calibrated, the results may be determined without predetermined cutoff using a relative color intensity difference between the control line and the test line. That is, by a scheme of comparing the final measurement value TI of the test area 1 and the final measurement value CI of the control area 3, the cutoff is not predetermined and is set at a ratio of CI value. For example, if the cutoff is set to be 90% of CI, the reaction may be set to be determined as a positive when the TI is over the cutoff and the reaction may be set to be determined as a negative when the TI is under the cutoff.

As described above, according to the present invention, the control area, the test area, and the background area are illuminated with light under the equivalent conditions and the light receiving units need to correspond to each area and the light receiving unit needs to be always arranged to be one more than the light source. By using the method, the device configured of at least two test areas illustrated in FIGS. 3 and 4 may accurately measure the analytes by calibration.

The invention claimed is:

1. A device for detecting an analyte in a sample comprising:
   (a) n light source units generating light comprising at least a first light source unit and a second light source unit, said n being equal or larger than integer 2;
   (b) a reaction strip including (i) a test area illuminated with the light from a light source unit and including a material reacting to the analyte, (ii) a control area illuminated with the light from a light source unit and including a control material, and (iii) a background area illuminated with the light from a light source unit, in which the test area and the background area are illuminated with a same one light from the first light source unit and the control area and the background area are illuminated with a same one light from the second light source unit; and
   (c) n+1 light receiving units detecting light emitted from the test area, the control area, and the background area of the reaction strip, respectively, and arranged to be in alignment with each of the test area, the control area, and the background area, respectively,
   wherein the emitted light detected is used for detection of the analyte in the sample;
   wherein the test area and the control area share the background area; and
   the first light source unit is positioned at an equal distance from the test area and the background area, and the second light source unit is position at an equal distance from the control area and the background area.

2. The device of claim 1, wherein the sample includes blood, plasma, serum, urine, lymph, bone marrow, saliva, milk, ocular fluid, semen, brain extracts, spinal fluid, synovial fluid, thymic fluid, ascites, amniotic fluid, cell tissue liquid, buffer solution, tap water, polluted water, sewage, or ground water.

3. The device of claim 1, wherein the material reacting to the analyte in the test area is a capture agent binding to the analyte.

4. The device of claim 3, wherein the capture agent is selected from the group consisting of an antibody, receptor, streptavidin, avidin, aptamer, lectin, DNA, RNA, ligand, coenzyme, inorganic ion, cofactor, sugar, and lipid.

5. The device of claim 1, wherein a number of the test area, the background area, or the test area and the background area is at least two.

6. The device of claim 5, wherein one of the at least two test areas and the control area share the background area.

7. The device of claim 1, further comprising: a processor for calibrating a value detected by the light receiving unit aligned for the background area to be a same value detected before a reaction by the light receiving units aligned for the test area and the control area.

8. The device of claim 7, wherein the processor additionally performs a process of calibration after a reaction at the test area and the control area employing a calibration constant obtained from the calibration before the reaction.

9. The device of claim 8, wherein the processor additionally performs a process of determining a value of an equation using calibrated values obtained before and after the reaction in the test area and the control area as a final measurement value of the test area and the control area.

10. The device of claim 9, wherein the processor additionally performs a process of comparing the final measurement value with a predetermined cut-off value to qualitatively determine whether the analyte is present in the sample.

11. The device of claim 9, wherein the processor additionally performs a process of substituting the final measurement value into a previously calculated quantification curve to quantitatively analyze the analyte in the sample.

12. The device of claim 1, wherein the device is a device for qualitatively or quantitatively detecting the analyte.

13. The device of claim 5, wherein the device is a device for multiplex detection to detect a plurality of analytes in the sample.

14. A method for detecting an analyte in a sample, comprising:
   (a) applying the sample to the device of claim 1;
   (b) obtaining a final measurement value of the test area and the control area from the light detected by the at least n+1 light receiving units of the device; and
   (c) determining whether the analyte is present in the sample or an amount of the analyte based on the final measurement value of the test area and the final measurement value of the control area obtained in (b),
   wherein the (b) obtaining a final measurement value comprises:
   calibrating a value detected by the light receiving unit aligned for the background area to be a same value detected before a reaction by the light receiving units aligned for each of the test area and the control area.

15. The method of claim 14, which further comprises:
   calibrating, after a reaction at the test area and the control area by employing a calibration constant obtained from the calibration before the reaction.

16. The method of claim 15, which further comprises:
   determining a value of an equation using calibrated values obtained before and after the reaction in the test area and the control area as a final measurement value of the test area and of the control area.

17. The method of claim 16, which further comprises:
   comparing the final measurement value with a predetermined cut-off value to qualitatively determine whether the analyte is present in the sample.

18. The method of claim 17, which further comprises:
   substituting the final measurement value into a previously calculated quantification curve to quantitatively analyze the analyte in the sample.

* * * * *